US011236442B2

(12) United States Patent
Francis et al.

(10) Patent No.: US 11,236,442 B2
(45) Date of Patent: Feb. 1, 2022

(54) ELECTROSPINNING APPARATUS AND METHODS OF USE THEREOF

(71) Applicant: LifeNet Health, Virginia Beach, VA (US)

(72) Inventors: Michael Francis, Virginia Beach, VA (US); Andy Pritchard, Virginia Beach, VA (US); Nathan Kemper, Virginia Beach, VA (US)

(73) Assignee: LIFENET HEALTH, Williamsburg, VA (US)

( * ) Notice: Subject to any disclaimer, the term of this patent is extended or adjusted under 35 U.S.C. 154(b) by 858 days.

(21) Appl. No.: 14/776,131

(22) PCT Filed: Mar. 13, 2014

(86) PCT No.: PCT/US2014/025601
§ 371 (c)(1),
(2) Date: Sep. 14, 2015

(87) PCT Pub. No.: WO2014/160002
PCT Pub. Date: Oct. 2, 2014

(65) Prior Publication Data
US 2016/0024690 A1 Jan. 28, 2016

Related U.S. Application Data

(60) Provisional application No. 61/786,196, filed on Mar. 14, 2013.

(51) Int. Cl.
*D01D 5/00* (2006.01)
*D01F 1/10* (2006.01)
*A61L 31/16* (2006.01)

(52) U.S. Cl.
CPC ............ *D01D 5/0084* (2013.01); *A61L 31/16* (2013.01); *D01D 5/0061* (2013.01); *D01D 5/0076* (2013.01); *D01D 5/0092* (2013.01); *D01F 1/10* (2013.01); *D10B 2331/041* (2013.01)

(58) Field of Classification Search
CPC .... A61L 31/16; D01D 5/0061; D01D 5/0076; D01D 5/0084; D01D 5/0092; D01F 1/10; D10B 2331/041
See application file for complete search history.

(56) References Cited

U.S. PATENT DOCUMENTS 9,803,294 B1 * 10/2017 Ren ...................... D01D 5/0076
10,415,156 B2 * 9/2019 Khandaker .......... D01D 5/0084
2009/0018643 A1 * 1/2009 Hashi ........................ A61F 2/82
623/1.15
2010/0183699 A1 7/2010 Wan et al.
(Continued)

FOREIGN PATENT DOCUMENTS

CN 101363137 2/2009
EP 2045375 A1 4/2009
(Continued)

OTHER PUBLICATIONS

International Search Report and Written Opinion dated Sep. 3, 2014; International Application No. PCT/US2014/025601.

*Primary Examiner* — Ryan M Ochylski
(74) *Attorney, Agent, or Firm* — RatnerPrestia

(57) ABSTRACT

The invention relates to an electrospinning apparatus and method of use thereof.

27 Claims, 8 Drawing Sheets

(56) References Cited

U.S. PATENT DOCUMENTS

| | | | | |
|---|---|---|---|---|
| 2011/0039101 A1* | 2/2011 | Chang | ............ | D01D 5/24 |
| | | | | 428/398 |
| 2012/0292795 A1* | 11/2012 | Peno | ............ | D01D 5/18 |
| | | | | 264/8 |
| 2014/0051316 A1* | 2/2014 | Zhang | ............ | D04H 1/74 |
| | | | | 442/401 |
| 2014/0079759 A1* | 3/2014 | Patel | ............ | A61L 27/50 |
| | | | | 424/443 |
| 2014/0207250 A1* | 7/2014 | O'Hare | ............ | A61L 27/34 |
| | | | | 623/23.72 |
| 2015/0086602 A1* | 3/2015 | Kipper | ............ | A61L 27/34 |
| | | | | 424/423 |
| 2016/0022865 A1* | 1/2016 | Francis | ............ | A61L 27/3604 |
| | | | | 424/569 |

FOREIGN PATENT DOCUMENTS

| | | |
|---|---|---|
| GB | 2427382 | 12/2006 |
| WO | 2007090102 | 8/2007 |
| WO | 2011095141 | 8/2011 |
| WO | 2011/159889 A2 | 12/2011 |
| WO | 2012078472 | 6/2012 |
| WO | 2013000442 | 1/2013 |

* cited by examiner

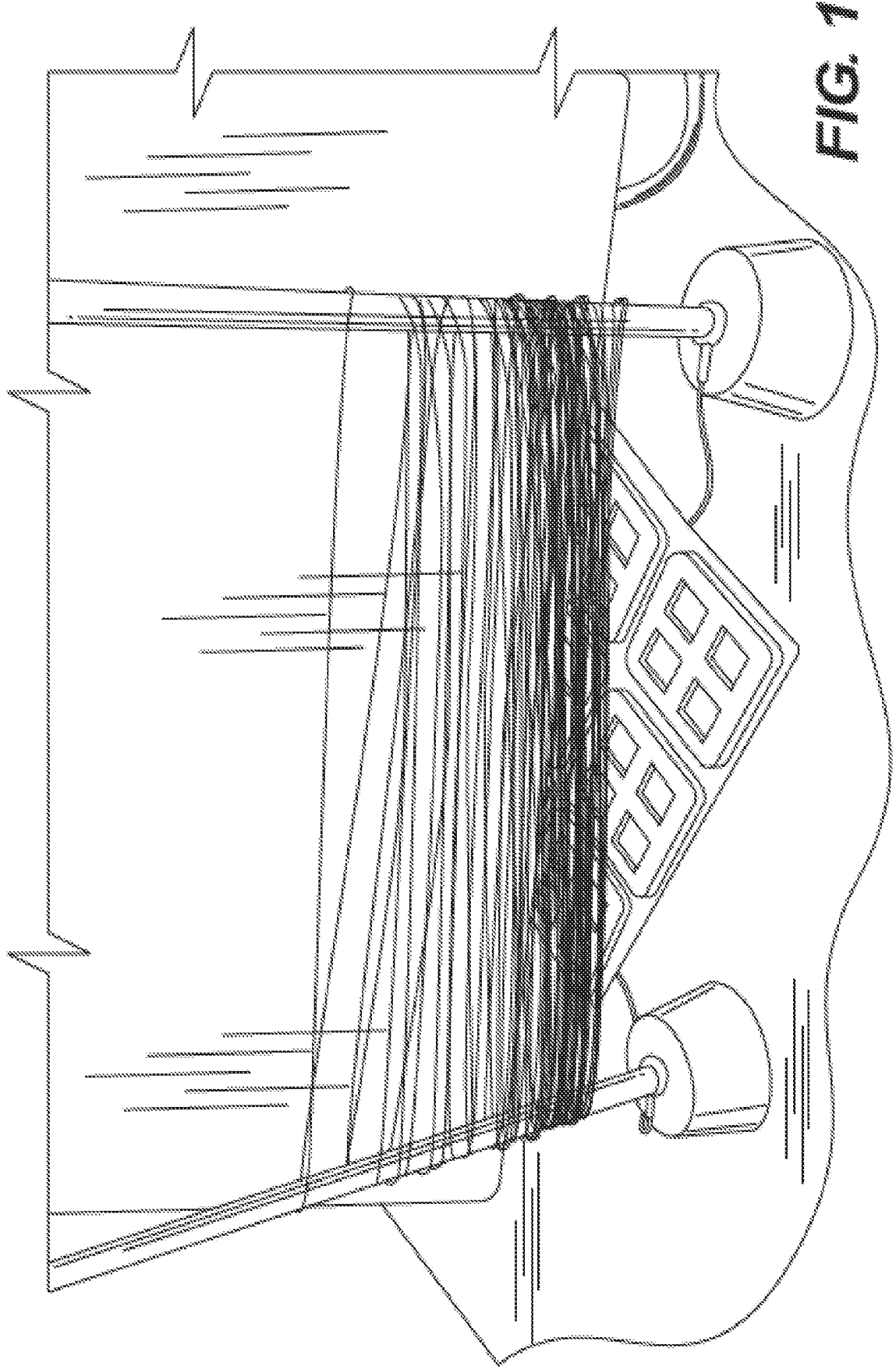

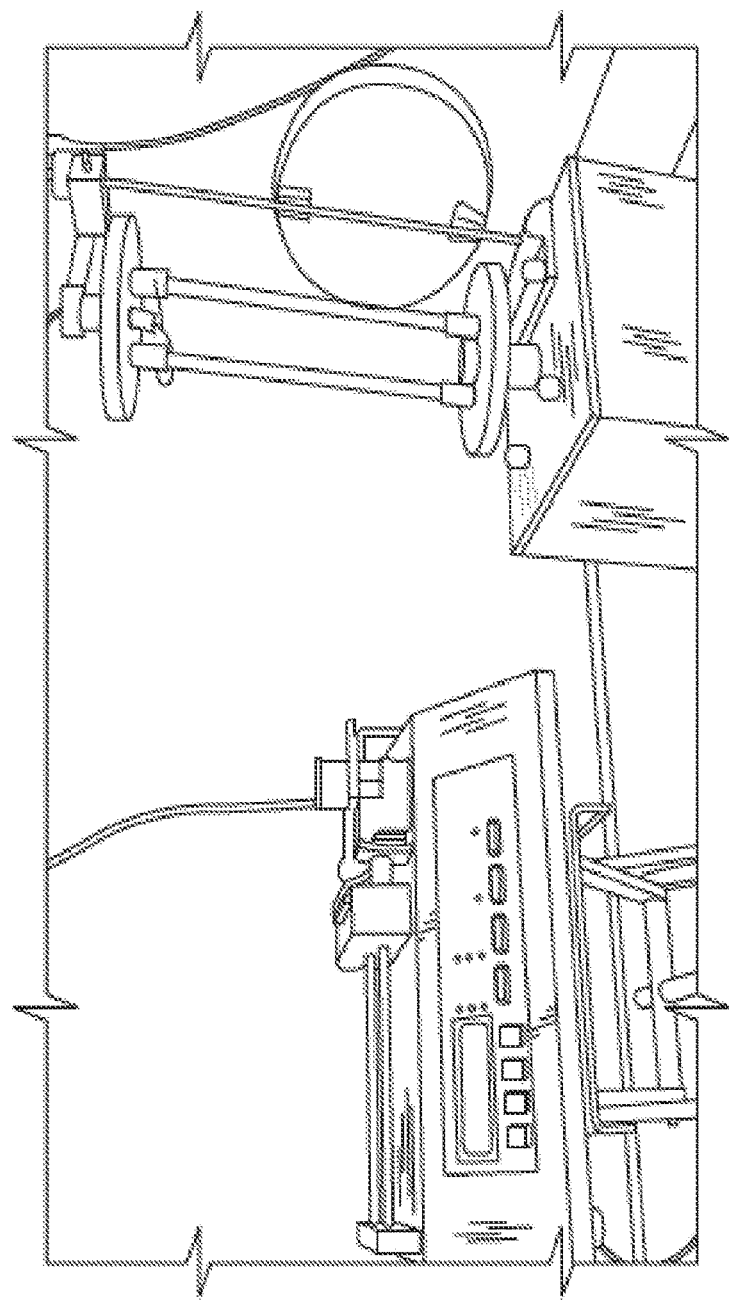
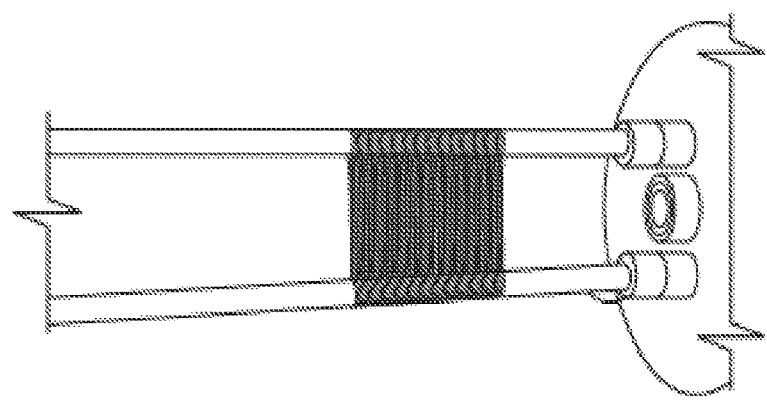
FIG. 6A
FIG. 6B

ELECTROSPINNING APPARATUS AND METHODS OF USE THEREOF

BACKGROUND OF THE INVENTION

The invention relates to an electrospinning apparatus and method of use thereof.

SUMMARY OF THE INVENTION

The invention relates to an electrospinning apparatus comprising (i) at least one spinneret comprising an electrified tip; and (ii) a collector comprising two rods and a platform connected to the two rods, wherein the two rods are configured split an electric field between them.

The invention also relates to an electrospinning apparatus comprising (i) two spinnerets, each of which comprises a tip electrified with an opposite charge to one another; and (ii) a collector comprising two rods and a platform connecting the two rods, wherein the two rods are grounded.

The invention further relates to methods of electrospinning using the electrospinning apparatus described herein.

The invention further relates to methods of preparing an electrospun fiber using the electrospinning apparatus described herein.

BRIEF DESCRIPTION OF THE DRAWINGS

FIG. 1 depicts metal rods that are used to align electrospun PCL. PCL dissolved in HFP (100 mg/ml) at a +15 kV reference, set 15 cm apart, is electrospun between the rods, with PCL pumped at 5 ml/hr over 5 minutes to the form the aligned nanofibers seen collecting between the rods.

FIG. 6 depicts the exemplary elements of the rotating parallel electric charged rod electrospinning setup in the left image. Using two charged rods imparts alignment to the traveling fibers, optionally through the point charge splitting of the electric field. A sheet of aligned fibers formed after 1 hour of electrospinning is shown on the right.

DETAILED DESCRIPTION OF THE INVENTION

Figure 2A:
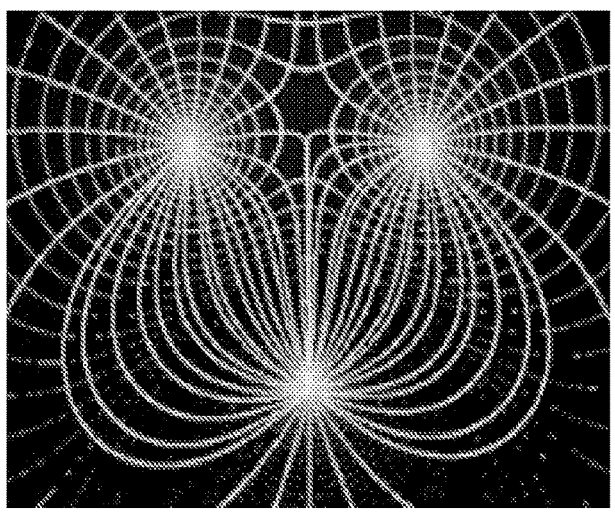
FIG. 2 depicts representative field lines that are modulated between a split point negative voltage sources and a single positive voltage source (A, D), aiding in imparting alignment in the electrospinning scheme. The change in field lines between a solid (B) and hollow (C) rod is also modeled.
Figure 2B:
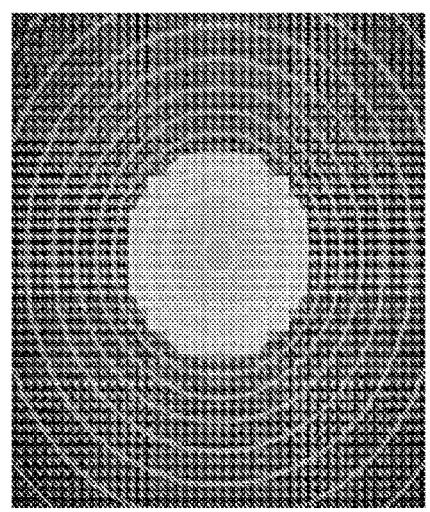
Figure 2C:
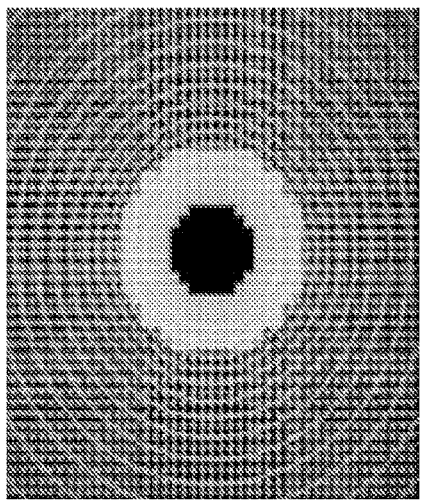
Figure 2D:
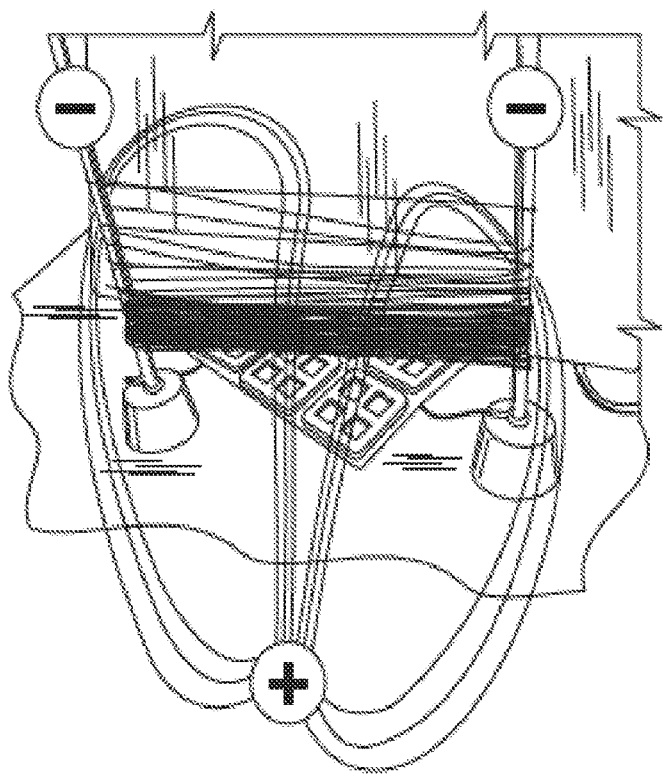

The invention relates to an electrospinning apparatus comprising (i) at least one spinneret comprising an electrified tip; and (ii) a collector comprising two rods and a platform connected to the two rods, wherein the two rods are configured split an electric field between them. In one aspect, the spinneret comprising an electrified tip may have two, three, four, five or more electrified tips. In another aspect, the collector comprising two rods may have three, four, five or more rods. In additional aspect, the platform connected to the two rods may have three, four, give or more rods connected to the platform. As defined herein, "comprising two rods" refers to comprising at least two rods, including, for example, two, three, four, and five rods.

The invention also relates to an electrospinning apparatus comprising (i) two spinnerets, each of which comprises a tip electrified with an opposite charge to one another; and (ii) a collector comprising two rods and a platform connecting the two rods, wherein the two rods are grounded.

Electrospray/electrospinning techniques can be used to form particles and fibers as small as one nanometer in a principal direction. The phenomenon of electrospray involves the formation of a droplet of polymer melt at an end of a needle, the electric charging of that droplet, and an expulsion of parts of the droplet because of the repulsive electric force due to the electric charges. In electrospraying, a solvent present in the parts of the droplet evaporates and small particles are formed but not fibers. The electrospinning technique is similar to the electrospray technique. In electrospinning and during the expulsion, however, fibers are formed from the liquid as the parts are expelled.

In particular, for example, the electrospinning typically involves a polymer solution (or melt) maintained at its surface tension on the tip of a nozzle via a syringe in a pump. When sufficiently high voltage is introduced (e.g. 15-40 kV) to the polymer or oligomer in solution to create a charge imbalance, the solution may be drawn towards a grounded collector through the static electric field. As the polymer erupts from the needle and the assembling polymer whip through space, the fiber may be subjected to a series of stretching and bending instabilities, resulting in plastic stretching and elongation to minimize these instabilities generated by repulsive electrostatic forces. As the polymer or oligomer travels through space and rapidly thins into a fine stream, the solvent may evaporate and the polymer or oligomer assembles into fibers, leaving dry nano- to microscale fibers of tailorable physical attributes on the collector in the typical electrospinning scheme. Additionally, when high electrical potential is applied to a low viscosity polymer or oligomer melt or solution, or when improperly high or low voltage is applied, electrospraying may occur, which is typified by the polymer jet breaking down into fine droplets. It is therefore possible to produce particles or nano- to micro-sphere particles, fibers and bead-and-string type structures via this process from simply altering the solution or electrospinning parameters. Polymer solution properties, applied electrical potential, polymer molecular weight, polymer solution flow rate, distance between spinner and collector, ambient parameters (e.g. humidity, air velocity, temperature) and motion of the collecting target can be altered to form fibers of controlled fiber distribution, diameter and alignment via electrospinning.

The electrospinning apparatus as described herein in one aspect may include one or more spinneret. The term "spinneret" used herein refers to a single- or multi-pored device through which a polymer or oligomer solution is extruded to form fibers. In one aspect, the spinneret is selected from the group consisting of a multiple nozzle spinneret, a single syringe or capillary spinneret, and a compound spinneret. In another aspect, the spinnerets of the electrospinning apparatus may be differently charged, resulting in differently charged polymer or oligomer solutions extruded from them. For example, different voltages may be applied to two or more polymer or oligomer sources whereby a positively charged solution is combined in space with a negatively charged solution, which is sent to the grounded rotating rods of the mandrel.

The electrospinning apparatus according to some embodiments of the present invention includes at least one spinneret comprising an electrified tip. The spinneret may have an electrified tip having a charge, and the tip may have one or more pores. In some embodiments, the electrospinning apparatus may include two or more tips having different charges. In particular, for example, the electrospinning apparatus may include two tips having opposite charges to each other.

In some embodiments, the spinneret described herein may be replaced with a different ejecting device comprising a drum configured to rotate in contact with a reservoir of a polymer or oligomer solution herein. In one aspect, this drum may pull the polymer or oligomer solution as a thin film on the surface of the drum. In another aspect, the drum may be charged, resulting in charging of the solution. In additional embodiments, the spinneret described herein may be replaced with a different ejecting device comprising a flat surface in contact with a polymer or oligomer solution, and the polymer or oligomer solution may form a polymer bubble(s) by applying air.

The electrospinning apparatus in one aspect may include a collector having at least two rods and a platform. In some embodiments, the collector may have, for example, three, four, five, six, seven, eight, nine, ten, twenty, thirty, or forty rods. Herein, the term "rod" used herein refers to a bar of material having a shape including, but not limited to prism, cylinder, pentagonal rod, hexagonal rod, square rod, and triangular rod. The rod may comprise an electrical conducting material (e.g. a metal). In some embodiments, the rod may be electrified with a charge opposite to a charge of the electrified tip extruding a solution to the rod. In another aspect, the rod may be made of a non-electrical conducting material (e.g. insulating plastic). In further aspect, the rod may be made of both electrical and non-electrical conducting materials. For example, the electrical conducting material may be coated on the non-electrical conducting material.

The rod described herein may be directly or indirectly connected and/or fixed to a platform. The platform refers to any support for the rod. In one aspect, the rod comprises a proximal part and distal end, and the proximal part and/or distal end may be connected and/or fixed to the platform. In another aspect, the rod may go through the platform to which the proximal part of the rod is connected and/or fixed.

In one aspect, the platform may be a part of a machine frame. In another aspect, the electrospinning apparatus described herein may further include a chamber enclosing the spinneret and the collector. The chamber may comprise the platform described herein. In another aspect, the platform may consist of or comprise a rotating shaft or a bearing that is directly or indirectly connected and/or fixed to the rod.

The platform according to some embodiments includes a bearing connected to the rod described herein. The bearing used herein refers to a guide for rotating the rod. In one aspect, the bearing may be a rotating shaft. In another aspect, the platform or the bearing used herein may use plain bearing, rolling-element bearings, jewel bearings, fluid bearings, magnetic bearings, and/or flexure bearings. The bearing may include an electrical conductor configured to allow electrical conductance to the rods. For example, the bearing may have mercury.

In another aspect, the platform connected to the rod(s) may be configured to spin resulting in rotation of the rod(s) about the spinning axis of the platform. In some embodiments, the rods are configured to rotate at between about 0 and about 8000 RPM, between about 0 and about 7000 RPM, between about 0 and about 6000 RPM, between about 0 and about 5000 RPM, between about 0 and about 4000 RPM, between about 0 and about 3000 RPM, between about 0 and about 2000 RPM, between about 0 and about 1000 RPM, between about 0 and about 500, between about 0 and about 300 RPM, between about 0 and about 100 RPM, between about 0 and about 50, between about 1 and about 2000 RPM, between about 1 and about 1000 RPM, between about 1 and about 500, between about 1 and about 300 RPM, between about 1 and about 100 RPM, between about 1 and about 50, between about 1000 and about 8000 RPM, between about 2000 and about 8000 RPM, between about 3000 and about 8000 RPM, between about 4000 and about 8000 RPM, between about 5000 and about 8000 RPM, between about 1000 and about 6000 RPM, between about 2000 and about 6000 RPM, or between about 3000 and about 6000 RPM. In additional embodiments, the rods are configured to rotate at about 50 RPM, about 500 RPM, about 1500 RPM, about 2500 RPM, about 3500 RPM, about 4500 RPM, about 5500 RPM, about 6500 RPM, about 7500 RPM or lower. In additional embodiments, the rods are configured to rotate at about 500 RPM, about 1500 RPM, about 2500 RPM, about 3500 RPM, about 4500 RPM, about 5500 RPM, about 6500 RPM, about 7500 RPM or higher. In some embodiments, when the rods are rotating, the fibers may spin around the rods. In other embodiments, when the rods are rotating, the fibers may also move or jump from one rod to another rod. In yet additional embodiments, the rods are stationary. In yet further embodiments, when the rods are stationary, the fibers may move or jump from one rod to another through an electric field.

In some embodiments, an air driven (pneumatic) motor and an electric (DC) motor may be employed in the electrospinning. In further embodiments, the pneumatic motor may generate less stray field anomalies and allow capturing of more nanofiber product on the rod(s) compared to the DC motor.

In one aspect, the fibers align on the rod (e.g. by spinning around the rods or jumping to one rod to another) in a perpendicular angle to the rods. In another aspect, the fibers align in an angle about 91, 92, 93, 94, 95, 100, 105, 110, 115, 120, 125, 130, 135, 140, 145, 150, 155° or less. In another aspect, the fibers align in an angle about 90, 91, 92, 93, 94, 95, 98, 103, 108, 113, 118, 123, 128, 133, 138, 143, 148, 153° or more. In another aspect, the fibers align in an angle between about 90 and about 93°, between about 90 and about 95°, between about 90 and about 100°, between about 90 and about 105°, between about 90 and about 110°, between about 90 and about 115°, between about 93 and about 95°, between about 93 and about 100°, between about 93 and about 105°, between about 93 and about 110°, or between about 93 and about 115°.

As used herein, the term "about" modifying, for example, the quantity of an ingredient in a composition, concentrations, volumes, process temperature, process time, yields, flow rates, pressures, and like values, and ranges thereof, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 10, 9, 8, 7, 6, 5, 4, 3, 2, 1 percent or less of the stated reference value.

The electrospinning apparatus according to some embodiments of the present invention includes a collector comprising two or more rods and a platform connected to the rods, wherein the rods are configured split an electric field between them. In one aspect, operating the electrospinning apparatus described herein may result in forming a point charge splitting of an electric field, through which traveling polymer or oligomer solutions align. In another aspect, the rods may be grounded.

The split electric field in some embodiments is separated by an air insulator. In one aspect, with air as an insulator between electrically charged metal rods, electrospun fibers are collect between opposed metal rods in an aligned fashion. The electrospun fiber described herein may be a microfiber or a nanofiber.

The split electric field in some embodiments is insulated by non-conductive materials or environments placed between the rods (e.g. carbon fiber, PTFE [Teflon], mica, diamond, ceramic, rubbers, glass, vacuum, materials on the low ends of the triboelectric series in the high resistivity range, also including paper, cotton, wood, epoxy, plastics such as: ABS [acrylonitrile, butadiene, and styrene], polycarbonate, acetate, acrylic, delrin, fiberglass, FEP, high impact polystyrene [HIPS], kapton, kaptrex, kynan, macor, melamine, meldin 7001 unfilled polyimide, MICA, neoprene, nomex, noryl PPO, PolyEtherEther-Ketone [PEEK], polyethylene terephthalate [P.E.T], P.E.T.G, phenolics such as micarta phenolics, perfluoroalkoxy [PFA], Polycarbonate, polyester [mylar], polyolefins, polystyrene, polysufone, polyurethane), Rexolite® 1422 &220, polyphenylene sulfide [Ryton], silicone/fiberglass, silicone rubber, techtron, Ultem® 1000, Vespel® SP-1 [polyimide], electrically insulating papers such as vulcanized fibre, tapes from the above materials, and foams of these materials, including neoprene foam, polystyrene foam, polyurethane foam, silicone foam, vinyl foam.

The term microfiber as used herein means a fiber comprising a diameter of about 1000 µm or less. The term nanofiber as used herein means a fiber comprising a diameter of about 1000 nm or less. Relative to the parent bulk material, nano-features can impart many extraordinary properties to macrostructures, including superior mechanical, electrical, optical and magnetic properties, adding surface functionality and yielding high surface area. Matrices of nanofibers of varying diameters may show a range of variable surface properties (e.g. hydrophobicity and hydrophilicity), porosities, and usually superior mechanical properties (e.g. tensile strength, stiffness) relative to the material in other forms.

In some embodiments, the nanofiber described herein may have an average diameter of about 1000 nm or less, 900 nm or less, 800 nm or less, 700 nm or less, 600 nm or less, 500 nm or less, 400 nm or less, 300 nm or less, 200 nm or less, 100 nm or less, 50 nm or less, 20 nm or less, or 10 nm or less.

In some embodiments, the microfiber described herein may have an average diameter of about 1000 µm or less, 900 µm or less, 800 µm or less, 700 µm or less, 600 µm or less, 500 µm or less, 400 µm or less, 300 µm or less, 200 µm or less, 100 µm or less, 50 µm or less, 20 µm or less, or 10 µm or less.

In some embodiments, the rods described herein may be set parallel to each other in the electrospinning apparatus. In other embodiments, the rods may not be set parallel to each other but at an angle, for example, at an angle smaller than 5°, 10°, 30°, 50°, 70°, or 90°. In other embodiments, the rods may not be set parallel to each other but at an angle, for example, at an angle bigger than 1°, 8°, 25°, 40°, 60°, or 75°. In additional embodiments, the rod described herein may be straight, curved or angled.

The rods described herein in some embodiments are separated from one another by an average distance of about 1 cm, about 2 cm, about 3 cm, about 5 cm, about 8 cm, about 10 cm, about 13 cm, about 15 cm, about 18 cm, about 20 cm, about 23 cm, about 25 cm, about 27 cm, about 30 cm or more. In one aspect, the rods are separated from one another by an average distance of about 1 cm, about 2 cm, about 3 cm, about 5 cm, about 8 cm, about 10 cm, about 13 cm, about 15 cm, about 18 cm, about 20 cm, about 23 cm, about 25 cm, about 27 cm, about 30 cm, about 40 cm, about 50 cm, about 60 cm or less. In another aspect, the rods are separated from one another by a distance from about 1 cm to about 25 cm, from about 6 cm to about 25 cm, from about 12 cm to about 25 cm, from about 18 cm to about 25 cm, from about 23 cm to about 25 cm, from about 1 cm to about 35 cm, from about 6 cm to about 35 cm, from about 12 cm to about 35 cm, from about 18 cm to about 35 cm, from about 24 cm to about 35 cm, or from about 10 cm to about 20 cm.

The collector may be biocompatible. In fact, any of the other elements of the electrospinning apparatus described herein may be biocompatible.

The electrospinning apparatus described herein may also include a control mechanism configured to control the electric potential of the electrified tip. The electrospinning apparatus described herein may also include a reservoir for a solution. The electrospinning apparatus described herein may also include an electric source connected to the electrified tip.

The invention further relates to methods of electrospinning using the electrospinning apparatus described herein and methods of preparing an electrospun fiber by the electrospinning. The methods of electrospinning and methods of preparing an electrospun fiber by the electrospinning may comprise (i) extruding a solution from an electrified tip of a spinneret, and (ii) collecting the extruded solution on at least a part of a collector. The methods of electrospinning or preparing an electrospun fiber by the electrospinning may further comprise extruding two, three or more solutions from one, two, three or more electrified tips of a spinneret. The methods of electrospinning or preparing an electrospun fiber by the electrospinning may further comprise extruding two, three or more solutions from one, two, three or more electrified tips of one, two, three or more spinnerets. The methods of preparing an electrospun fiber by the electrospinning may further comprise coating the extruded solution with another electrospun fiber prepared by the methods described herein.

The solution that may be extruded using the electrospinning apparatus described herein may include, but is not limited to, solutions comprising collagen type I, adipose extracellular matrix, heart basement membrane extract or extracellular matrix, placenta basement membrane extract or extracellular matrix, and polycaprolactone. Additional materials that may be electrospun by the method described herein include, but are not limited to, poly(glycolic acid), poly(lactic acid), polydioxanone, poly(lactide-co-glycolide) copolymers, polyesters polysaccharides, polyhydroxyalkanoates, starch, polylactic acid, cellulose, proteins, agar, silks, alginate, collagen/gelatin, carrageenan, elastin, pectin, resilin, konjac, adhesives, gums, polyamino acids, polysaccharides, soy, zein, wheat gluten, casein, chitin/chitosan, serum albumin, hyaluronic acid, lipids/surfactants, xanthan, acetoglycerides, waxes, surfactants, dextran, emulsan, gelian, polyphenols, levan, lignin, curd, ian, tannin, polygalactosamine, humic acid, shellac, pullulan, poly-gamma-glutamic acid, elsinan, natural rubber, yeast glucans, and synthetic polymers from natural fats and oils, and the mixture thereof.

In one aspect, the collector of the electrospinning apparatus is a biocompatible support to be coated by the electrospun fiber on its surface and may be used as a part of the implant described herein. For example, the collector may comprise a bone matrix, and the electrospun fiber is collected on the surface of the bone matrix, resulting in coating of the bone matrix. The bone matrix may have two or more different electrospun fiber coatings on its surface.

The invention further relates to a method of coating a matrix on a surface comprising (i) extruding a solution from an electrified tip of a spinneret, and (ii) collecting the extruded solution on a portion of a collector, wherein the collector further comprises two rods and a platform connected to the two rods, the two rods are configured to split an electric field between them, and the portion of the collector comprises the matrix. The invention further relates to a method of coating a matrix on a surface comprising (i) extruding one or more solutions from electrified trips of two spinnerets, each of which comprises at least one tip electrified with an opposite charge to a tip of the other spinnerets, and (ii) collecting the extruded solution on a portion of a collector, wherein the collector further comprises two rods and a platform connected to the two rods, the two rods are grounded, and the portion of the collector comprises the matrix. In some embodiments, the matrix is a bone matrix, and the solution is a bone matrix solution. In additional embodiments, the matrix may comprise a synthetic surface.

In some embodiments, the matrix is biocompatible. In further embodiments, the biocompatible matrix is an implantable biocompatible matrix that can function as a support system for the bone matrix described herein. A biocompatible matrix should be non-toxic, non-eliciting or stimulating severe inflammatory response or immunological rejections, and devoid of other undesired reactions at the implantation site. In one embodiment, the biocompatible matrix is bone matrix or cartilage or connective tissue.

In some embodiments, the biocompatible matrix includes but is not limited to, bone graft implants, synthetic bone graft materials in forms of particulates, sheet, or blocks, tendon and/or ligament in bone tunnels, prosthetic implant, for example, for hip, shoulder, knee, or ankle, and trabecular metal. In further embodiments, the bone graft implants may include allograft or xenograft. In yet further embodiments, the bone graft implants may include structural bone implants including, but not limited to, monolithic or composite spinal implants (e.g., VERTIGRATs from LifeNet Health) and bone struts or blocks. In yet further embodiments, the bone graft implants may include demineralized, or non-demineralized bone particulates, including, but not limited to, cortical, cancellous, or cortical cancellous bone. In other embodiments, the electrospun fibers may be formed on cell or tissue culture surface.

Suitable biocompatible matrices include, but are not limited to, porous biocompatible scaffolds into which bone cells or progenitor cells may migrate. Osteogenic or chondrogenic cells, i.e., cells involved in the process of deposition of new bone material or cartilagenous material, respectively, can often attach to such porous biocompatible matrices, which can then serve as scaffolding for bone and cartilage tissue growth. Cells involved in the process of deposition of new ligament or tendon material can also attach to such porous biocompatible matrices. For certain applications, the biocompatible matrix should have sufficient mechanical strength to maintain its three dimensional structure and help support the immobilization of the bone segments being united or grafted together. Porous biocompatible matrices which provide scaffolding for tissue growth can accelerate the deposition of new bone or the rate of bone growth and are said to be "osteoconductive." Osteoconductive biocompatible matrices are especially useful in the matrices described herein. Porous biocompatible matrices which provide scaffolding for tissue growth can accelerate the deposition of new cartilage or the rate of cartilage growth and are said to be "chondroconductive." Osteoconductive biocompatible matrices are especially useful in the matrices described herein. Chondroconductive biocompatible matrices are especially useful in the matrices described herein. Angiogenic (or vasculogenic) biocompatible matrices are especially useful in the pharmaceutical compositions described herein. The osteoinductive, angiogenic or chondroinductive activity of the surface coated with the electrospun fibers or may not be altered, including but not limited to, enhanced activity, relative to a surface without the electrospun fiber coating or a natural surface without any coating. Thus, the osteoconductive, angiogenic or chondroconductive activity of the biocompatible matrices treated with the electrospun fibers of the present invention may be enhanced compared to matrices not treated with the bone matrix described herein. Of course, the biocompatible matrices are considered to be osteoconductive, angiogenic or chondroconductive if cells within the biocompatible matrix begin to differentiate into more osteoblast-like or chondrocyte-like appearing or functional cells, respectively.

The biocompatible matrices according to some embodiments of the present invention can be derived from natural sources or they can be synthetic or a mixture of both. Biocompatible matrices from natural sources may also comprise natural polymers, including, but not limited to, collagen, hyaluronic acid, alginate, albumin, fibrinogen-fibrin, chitosan, elasin, laminin, connective tissues, intervertebral disc, cortical or cancellous bone, demineralized or mineralized bone, fascia lata, dermis, muscle, ligament, tendon, cartilage including articular/hyaline cartilage, elastic cartilage, and fibrocartilage, a mixture thereof, and mixture of reconstituted tissue. Biocompatible matrices from synthetic sources refer to any material not produced by living organisms, which may include, not limited to, the synthetic material made up of organic components, inorganic components, or a mixture thereof. In some embodiments, a synthetic biocompatible matrix may comprise an organic synthetic polymer, such as poly(lactic-co-glycolic acid), polycaprolactone (PCL), polyglycolic acid (PGA), polylactic acid (PLA), polyhydroxybutyrate (PHB), Poly(ethylene glycol) (PEG), poly(ethylene oxide) (PEO)), and others. In some embodiments, a tissue, an organ, or biocompatible matrix comprising at least one of alginate, chitosan, collagen, gelatin, hyaluronic acid, a fibronectin, an elastin, a laminin, and a proteoglycan may be employed. In certain embodiments, a biocompatible matrix comprising inorganic components, such as hydroxyapatite, calcium sulfate, octacalcium phosphate, calcium phosphate, macroporous calcium metaphosphate ceramic, β-tricalcium phosphate, metal, metal alloy, and others, may be used. A biocompatible matrix used in certain embodiments of the present invention may be prepared by demineralizing, decellularizing or devitalizing a tissue or an organ and cells may be seeded onto the biocompatible matrix.

In some embodiments, the electrospun fibers described herein may be applied to a biocompatible matrix and may be incubated at conditions permitting the generation of a matrix that is partially or fully coated with the electrospun fibers. In some embodiments, incubation may be carried out at about 40° C. or lower, or between about 10° C. and about 37° C., or about 20° C. and about 37° C. Incubation may be carried out for between at least about 2 minutes and about 120 minutes, about 3 minutes and about 100 minutes, about 4 minutes and about 80 minutes, about 5 minutes and about 60 minutes, and about 5 minutes and about 30 minutes in certain embodiments. Incubation may be performed under static or dynamic conditions, such as with agitation, shaking, stirring, mixing, horizontal motion, rocking, and others.

In some embodiments of the present invention, a biocompatible matrix may be lyophilized before the electrospun fiber is applied to the biocompatible matrix. In certain embodiments, the electrospun fibers may be coated on the biocompatible matrix, and the coated matrix may be subsequently lyophilized. The lyophilized, coated matrix can then be rehydrated before it is used. Further, the cells can be seeded onto the matrix before implantation.

Examples of suitable osteoconductive or chondroconductive biocompatible matrices include but are not limited to, collagen (e.g., bovine dermal collagen), fibrin, calcium phosphate ceramics (e.g., hydroxyapatite and tricalcium phosphate), calcium sulfate, guanidine-extracted allogenic bone and combinations thereof. A number of suitable biocompatible matrices are commercially available, such as Collograft™ (Collagen Corporation), which is a mixture of hydroxyapatite, tricalcium phosphate and fibrillar collagen, and Interpore™ (Interpore International), which is a hydroxyapatite biomatrix formed by the conversion of marine coral calcium carbonate to crystalline hydroxyapatite.

A number of synthetic biodegradable polymers can serve as osteoconductive or chondroconductive biocompatible matrices with sustained release characteristics. Descriptions of these polymers can be found in Behravesh (1999) Clinical Orthopaedics 367, S118 and Lu (2000) Polymeric Delivery Vehicles for Bone Growth Factors in Controlled Drug Delivery: Designing Technologies for the Future, Park and Mrsny eds., American Chemical Society, which is incorporated herein in its entirety herein. Examples of these polymers include poly α-hydroxy esters such as polylactic acid/ polyglycolic acid homopolymers and copolymers, polyphosphazenes (PPHOS), polyanhydrides and poly(propylene fumarates).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson (1997) Adv. Drug Deliv. Rev. 28:5. The incorporation of PEG into the polymer as a blend to form microparticle matrices allows further alteration of the release profile of the active ingredient (see Cleek (1997) J. Control Release 48, 259). Ceramics such as calcium phosphate and hydroxyapatite can also be incorporated into the formulation to improve mechanical qualities.

In one embodiment, the biocompatible matrices used in the methods of the present invention are other types of bone matrices. For example, the electrospun fibers prepared by the methods described herein can be coated on a bone matrix. As used herein, the other types of the bone matrix may be a biocompatible matrix derived from or including elements of natural bone. In some embodiments, the natural bone is mineralized, partially demineralized, demineralized, cancellous, cortical, or cortical cancellous bone. The bone matrices used herein may or may not include additional synthetic components not typically found in bone tissue. Other embodiments include methods utilizing a biocompatible matrix derived from cartilage, other soft tissues such as the dermis, connective tissue, fascia, small intestine submucosa, serous membrane, pericardium, tendon, ligament, muscle, adipose tissue, myelin, blood vessels, base membrane, amniotic membrane and others. A biocompatible matrix prepared from hyaline cartilage, fibrocartilage or elastic cartilage, may be employed in some embodiments. A biocompatible matrix may be prepared from hyaline cartilage found in the condyle, tibial plateau, femoral head, humeral head, costal cartilage, or fibrocartilage found in intervertebral discs, or elastic cartilage found in the epiglottis or ear. In certain embodiments, a biocompatible matrix derived from natural sources that has been optionally cleaned, disinfected, chemically modified, decellularized, particulated, homogenized, lyophilized, gamma ray irradiated, and/or plasticized may be used. Any of the biocompatible matrices used herein may or may not include additional synthetic components not typically found in such tissue.

In one specific embodiment, the bone or cartilage biocompatible matrices may be demineralized or decellularized, respectively. Examples of demineralized matrices and methods of making are described in U.S. Pat. Nos. 6,189, 537 and 6,305,379, which are incorporated herein in its entirety herein.

The biocompatible matrix, tissue, or organ used in certain embodiments of the present invention may be in the form of a powder, particulates, sheets, fibers, gels, putties, paste, blocks, cylinders, sponges, meshes, films, slices, curls, flakes, or wedges, among others. In certain embodiments of the present invention, the biocompatible matrix, tissue, or organ treated with the electrospun fibers by the methods described herein may be in the form of a powder, fibers, putty, or a sponge. In further embodiments, the sponge can include, for example, the implant having sponge-like structures disclosed in the co-pending, commonly-assigned patent application PCT/US09/04556 entitled "Composition for a Tissue Repair Implant and Methods of Making the Same"

filed on Aug. 7, 2009, which is incorporated herein in its entirety herein. The treated matrices can be used in any of the methods of the present invention.

The invention also related to a method of preparing an electrospun fiber by electrospinning comprising (i) extruding a solution from an electrified tip of a spinneret, and (ii) collecting the extruded solution on a portion of a collector comprising two rods and a platform connected to the two rods, wherein the two rods are configured to split an electric field between them. The invention further related to a method of preparing an electrospun fiber by electrospinning comprising (i) extruding one or more solutions from electrified trips of two spinnerets, each of which comprises at least one tip electrified with an opposite charge to a tip of the other spinnerets, and (ii) collecting the extruded solution on a part of a collector comprising two rods and a platform connecting the two rods, wherein the two rods are grounded. In some embodiments, the method of preparing an electrospun fiber further comprises applying an accessory polymer to the solution (e.g. as a copolymer, blend, or melt). An "accessory polymer" refers to a polymer that may be added to the electrospun fibers and have any effect on their physical, chemical, and/or biological properties (e.g. tensile strength, hydrophillicity, biocompatibility). For example, the accessory polymer may be selected from the group consisting of polycaprolactone, poly(glycolic acid), poly (lactic acid), polydioxanone, poly(lactide-co-glycolide) copolymers, polyesters polysaccharides, polyhydroxyalkanoates, starch, polylactic acid, cellulose, proteins, agar, silks, alginate, collagen/gelatin, carrageenan, elastin, pectin, resilin, konjac, adhesives, gums, polyamino acids, polysaccharides, soy, zein, wheat gluten, casein, chitin/chitosan, serum albumin, hyaluronic acid, lipids/surfactants, xanthan, acetoglycerides, waxes, surfactants, dextran, emulsan, gelian, polyphenols, levan, lignin, curd, ian, tannin, polygalactosamine, humic acid, shellac, pullulan, poly-gammaglutamic acid, elsinan, natural rubber, yeast glucans, and synthetic polymers from natural fats and oils.

In one aspect, the method of preparing the electrospun fiber(s) according to some embodiments of the present invention may further comprise crosslinking the electrospun fiber(s). In some embodiments, the crosslinking may be performed by any conventional chemical crosslinking method (e.g. chemical reagent-promoted, chemically reactive linker-promoted and/or enzyme-promoted) and/or dehydrothermal crosslinking method (e.g. heat-promoted condensation), forming the covalently crosslinked electrospun fiber(s). In additional embodiments, the crosslinking comprises applying a cross-linking agent to the polymer or oligomer solutions to be electrospun. For example, the cross-linking agent may be selected from the group consisting of 1-Ethyl-3-(3-dimethylaminopropyl)carbodiimide (EDC), EDC/hyaluronic acid, genipin, and glutaraldehyde.

In some embodiments, a method of preparing an electrospun fiber further comprises adding a bioactive factor to the solution. A "bioactive factor" refers to protein, carbohydrate, or mineral that has any effect on a cellular activity. Examples of bioactive factors include, but are not limited to, an osteogenic growth factor, collagen, glycosaminoglycans, osteonectin, bone sialo protein, an osteoinductive factor, a chondrogenic factor, a cytokine, a mitogenic factor, a chemotactic factor, a transforming growth factor (TGF), a fibroblast growth factor (FGF), an angiogenic factor, an insulin-like growth factor (IGF), a platelet-derived growth factor (PDGF), an epidermal growth factor (EGF), a vascular endothelial growth factor (VEGF), a nerve growth factor (NGF), a neurotrophin, a bone morphogenetic protein (BMP), osteogenin, osteopontin, osteocalcin, cementum attachment protein, erythropoietin, thrombopoietin, tumor necrosis factor (TNF), an interferon, a colony stimulating factor (CSF), stem cell derived factor-1 (SDF-1), or an interleukin, among others. The bioactive factor may be a BMP, PDGF, FGF, VEGF, TGF, insulin, among others. Examples of BMPs include but are not limited to BMP-2, BMP-3, BMP-4, BMP-5, BMP-6, BMP-7, BMP-8, BMP-9, BMP-10, BMP-11, BMP-12, BMP-13, BMP-14, BMP-15, truncated BMPs described in PCT/US2012/053584, which is incorporated by reference in its entirety herein, and a mixture thereof.

The following examples are illustrative and are not intended to limit the scope of the invention described herein.

EXAMPLES 1,1,1,3,3,3-hexafluoro-2-propanol (HFP) (CAS #920-66-1) was from Acros Organics (Geel, Belgium, acros.com). Polycaprolactone (PCL) (B6003-1, B6003-2) was from Durect Lactone (Pelham, Ala., absorbables.com). The electrospinning apparatus was designed using an Aladdin Programmable Syringe Pump from World Precision Instruments, Inc. (Sarasota, Fla., wpiinc.com) and two adjustable high voltage power supplies from Gamma High Voltage Research (Ormond Beach, Fla.). The aligned metal rods used in the rotating motor, or statically, can be of steel, stainless steel, copper, or other heavy metal, as used in the illustrated drawing in FIG. 5. A Mercotac® connector (#110T and 110TS) was used as an electrically conductive bearing. The following items were purchased from McMaster-Carr:

8965K42 Ultra Conductive Copper (Alloy 101) Rod, ¼" Diameter

1256T14 Multipurpose Stainless Steel (Type 304) Mirror Finish #8, ¼" Diameter

88855K51 High-Strength Stainless Steel (Type 17-4 Ph) ¼" Diameter

86985K31 High-Strength Aluminum (Alloy 2024) ¼" Diameter

8965K86 Ultra Conductive Copper (Alloy 101) Tube, ¼" OD, 0.186" ID, 0.032" Wall Thk 8457K536 Stainless Steel Shape Type 304/304L, Round Tube, ¼" OD 1968T11 High-Strength Aluminum Tube (Alloy 2024) ¼" OD, 0.180" ID, 0.035" Wall Thickness 2706A4 Tube Cutter ¼" to 1⅝" Tube OD, 6" Open/Closed Length 4575N3 Miniature Flange-Mounted SS Ball Bearing Shielded, for ¼" Shaft Diameter 6384K352 Steel Ball Bearing Flanged Double Sealed for ¼" Shaft Dia, ¹¹⁄₁₆" OD 8600N3 Miniature Alum Base-Mnt SS Ball Brng—ABEC-3 for ¼" Shaft Diameter 7200K3 NEMA 34 Face-Mount Brushless DC Motor ⅓ hp, 3450 rpm, Integrated Speed Control 6099K41 Stainless Steel One-Piece Set-Screw Coupling ½" Bore, 1½" Length, 1" OD, with Keyway 8774K33 Static-Dissipative Clear Cast Acrylic Sheet ¼" Thick, 12"×24"

97042A516 18-8 Stainless Steel One-End Threaded Stud ½"-13×⅝"×1½"

99223A067 Acetal Hex Nut ½"-13 Thread

94564A023 Nylon Flat Point Socket Set Screw 6-32×¼"

9986K21 Black Delrin Rod 4" Diameter, ½" Length

8576K15 Black Delrin Rod ½" Diameter, 5' Length

94922A050 Nylon 6/6 Acorn Nut Off-White, ½"-13 Thread Size, ¾" W, 13/16" H
8572K61 White Delrin Rod 1" Diameter, 1' length
8582K21 White Delrin Rod 4" Diameter, ½" Length
8572K55 White Delrin Rod ½" Diameter
93140A839 Polycarbonate Machine Screw Flat Head Slotted, ¼"-20×¾"
95868A148 Nylon 6/6 SHCS 6-32 Thread, ½" Length, Off-White
7643A421 1"×30', Gray, 0.012" Thk, High-Temp Self-Fusing Silicone Rubber Tape
7586K12 Adhesive-Backed Cable Holder Press in, ¼" Maximum Bundle
60015K42 Tear-Resistant Rubber Vibration Damping Pad 6"×6"×⅜" Thick, 45 PSI Max Load
4056K42 Oil-Resistant Nitrile Vibration Damping Pad 6"×6"×5/16" Thick, 100 PSI Max Load
94605A541 Nylon 82 Deg Flat Head Slotted Machine Screw ¼"-20×¾"
94564A080 Nylon Flat Point Socket Set Screw ¼"-20×½"
5537K26 Tinned Copper Expandable Mesh Sleeving ¼" ID, 3/16" to 5/16" Bundle Dia
8491A614 Steel Press-Fit Drill Bushing/Liner 0.257" (F) ID, 13/32" OD, ½" Length
3504T21 Push-on Round FDA Cap Fits ⅜" OD, ½" Inside Height
92805K22 Push-on High-Temperature Silicone Rubber Cap Fits 0.6" Outside Diameter, 1½" Inside Height A high voltage power supply source was used to apply a +10-40 kV DC voltage to parallel metal rods, with a −5-40 kV DC field applied to the syringe/needle containing a polymer solution, with syringe placed in a syringe pump. The metal posts can be hollow or solid, and have been tested as rods of stainless steel, steel, copper, and aluminum, both solid and hollow using thin-walled tubing. The absolute DC field strength ranged from 15 kV to 60 kV. A programmable syringe pump was set to dispense the solution at 0.50-9.50 mL/hr, ideally at 6.5 ml/hr for pure PCL, and 3 ml/hr for heart basement membrane (HBM) and HBM/PCL mixtures. After approximately 5 minutes to 1 hour of electrospinning, the aligned fibers are collected for imaging (SEM and DIC).

A photo of electrospun PCL is seen collecting across steel rods set 20 cm apart in FIG. 1, with FIG. 2 (a, d) showing the representative electric field lines and the know bending of these lines in a field with a split point charge (as simplified plane of point charges represented). This splitting of the electric charge field is believed to act on imparting alignment as they travel on the looping fibers in this warped electrostatic field. We have successfully aligned fibers with hollow and solid metal rods, and the modulation of the electric field lines by solid vs. hollow rods is also shown (FIG. 2b, 2c) (electric field diagrams created using the applet from cco.caltech.edu/~phys1/java/phys1/EField/EField.html).

Figure 3:
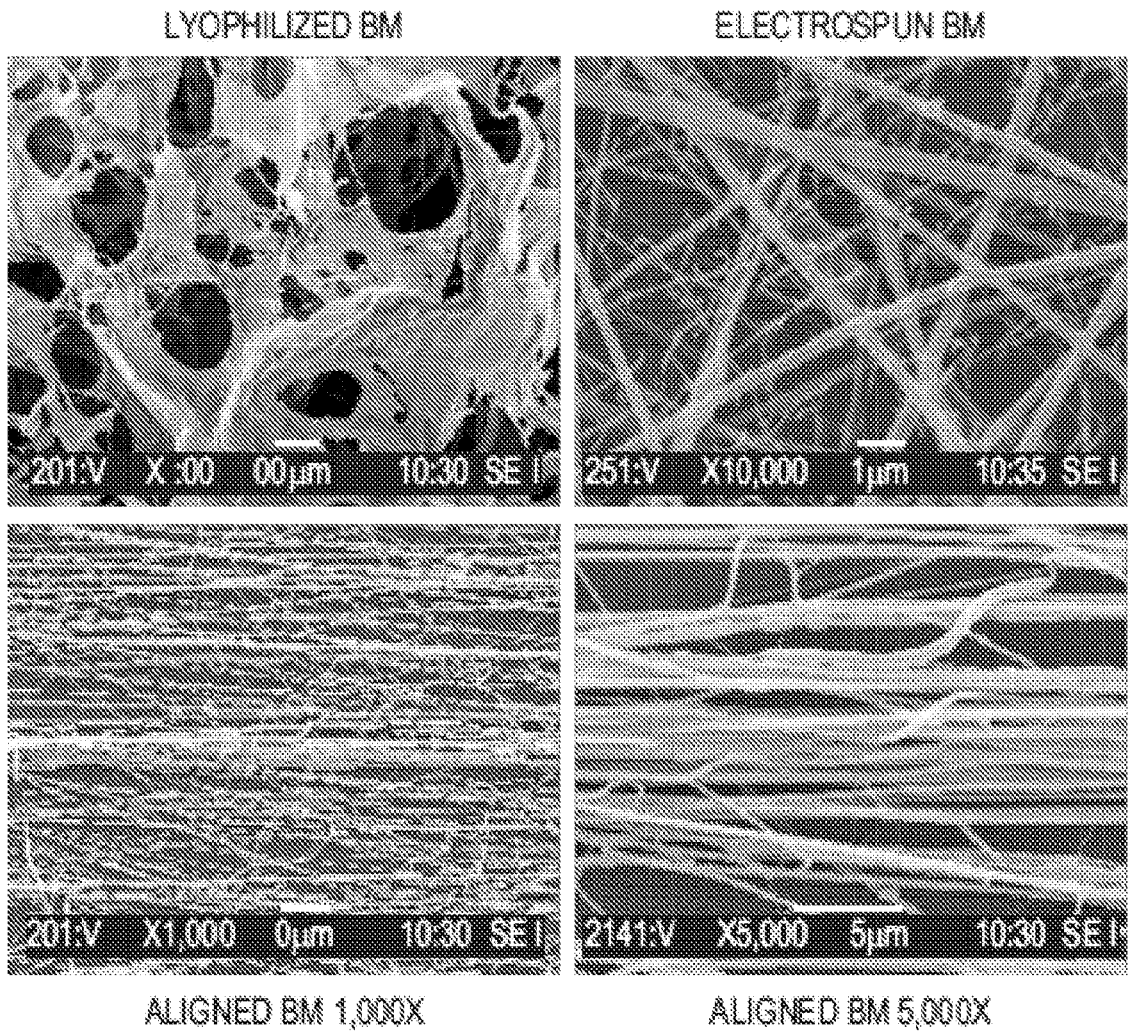
FIG. 3 depicts raw basement membrane (top left) next to it randomly electrospun architecture (to right), as compared to aligned basement membrane generated by parallel charged rod aligned electrospinning (bottom left and right).
Figure 4B:
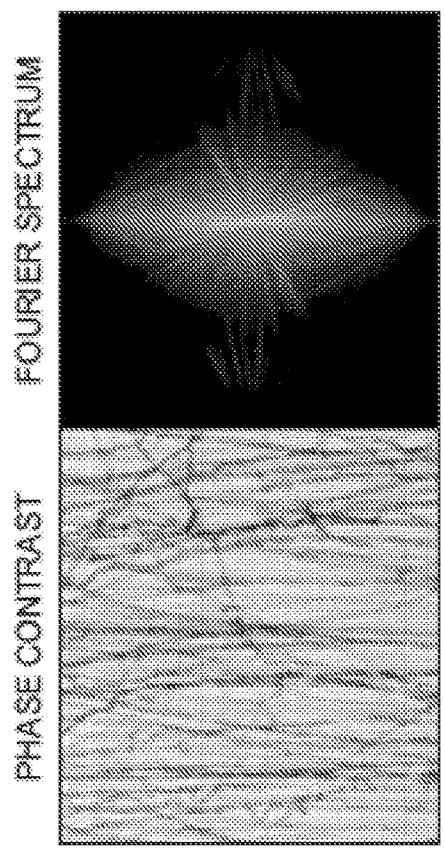
FIG. 4 depicts a Fourier spectrum from charged rod aligned and randomly electrospun fibers. The aligned pattern/texture recognition is typical to that of a regular, repeating line pattern, with the random fibers consistent with random noise generation spectra, as commonly seen in pattern recognition from FFT analysis.
Figure 4A:
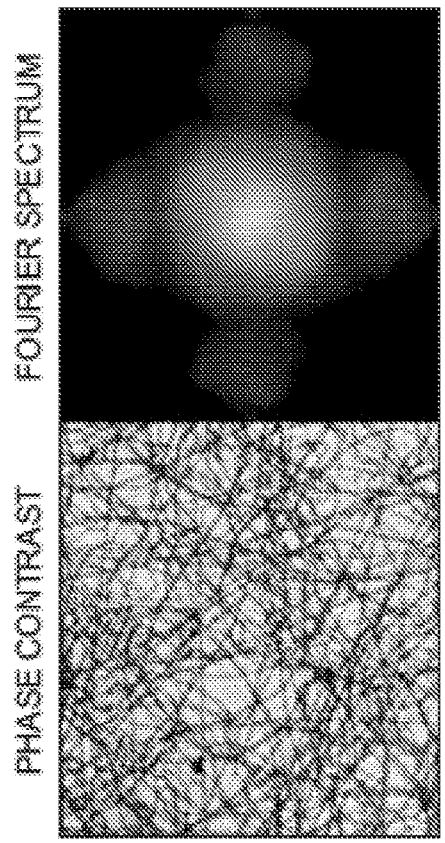

For SEM images, aligned electrospun PCL and HBM/PCL blended samples were taken from the aligned rods and mounted on aluminum stubs using carbon stickers. The samples were then coated with gold at about 50 nm thickness using a plasma-based sputter coater. Coated samples were imaged using a JOEL 6400 scanning electron microscope (SEM) with Orion image processing. Representative images of charged parallel rod aligned fibers, as compared to fibers generated in the traditional, randomly aligned fashion by collection onto a static piece of grounded foil, can be seen in FIG. 3. The average cross-sectional fiber diameter of the electrospun fibers generated from random and charged rod aligned basement membrane matrix was calculated by measuring 35 unique points in ImageJ64 (NIH shareware), with results shown in FIG. 3, along with the average angle of the fibers. A fast Fourier transform (FFT) was performed to indicate the degree of alignment as seen in FIG. 4 using the ImageJ64 FFT tool, with patterns of aligned fibers shown to match with those of know aligned Fourier spectra, as commonly used for pattern recognition.

Figure 5C:
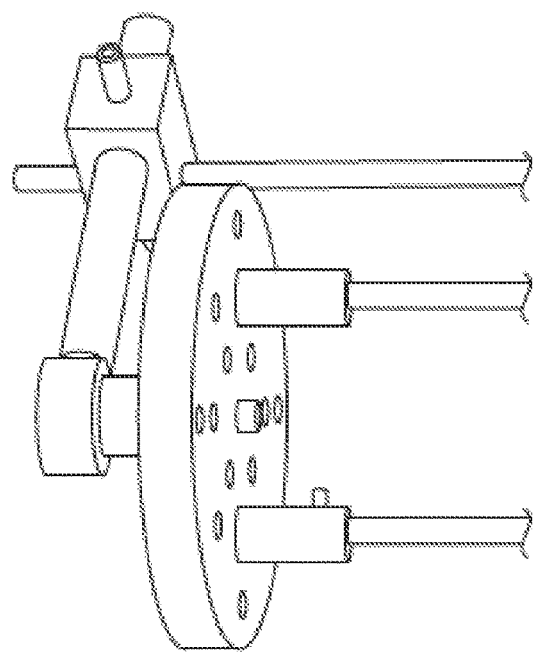
FIG. 5 depicts a modeling of a rotating parallel rod mandrel having a mercury coupled bearing inserted into the top of the device to split the electrical charge between the rods.
Figure 5B:
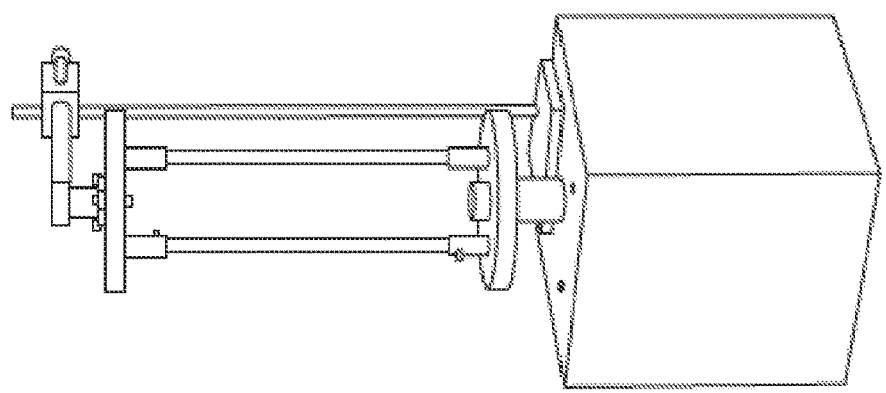
Figure 5A:
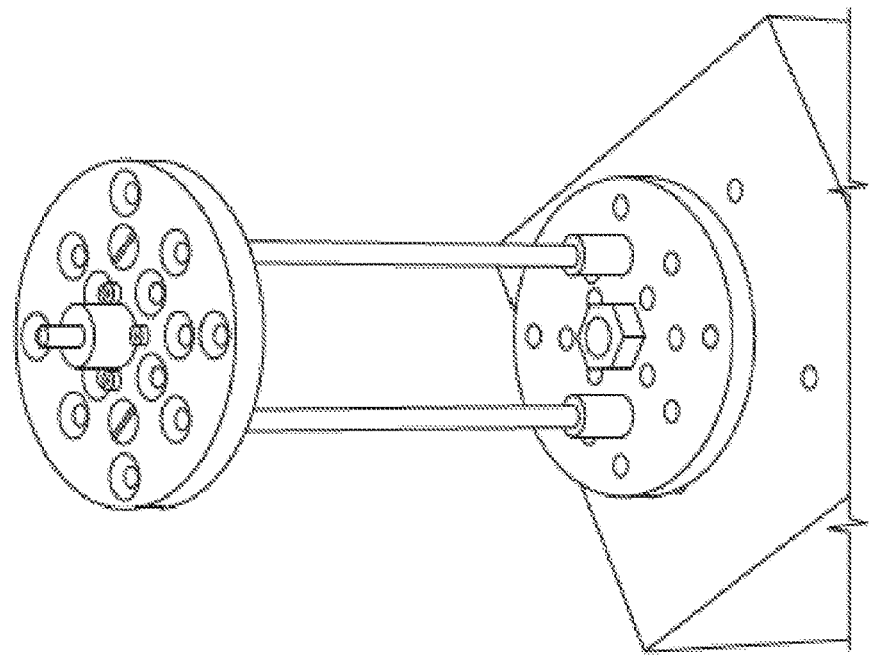
Figure 7:
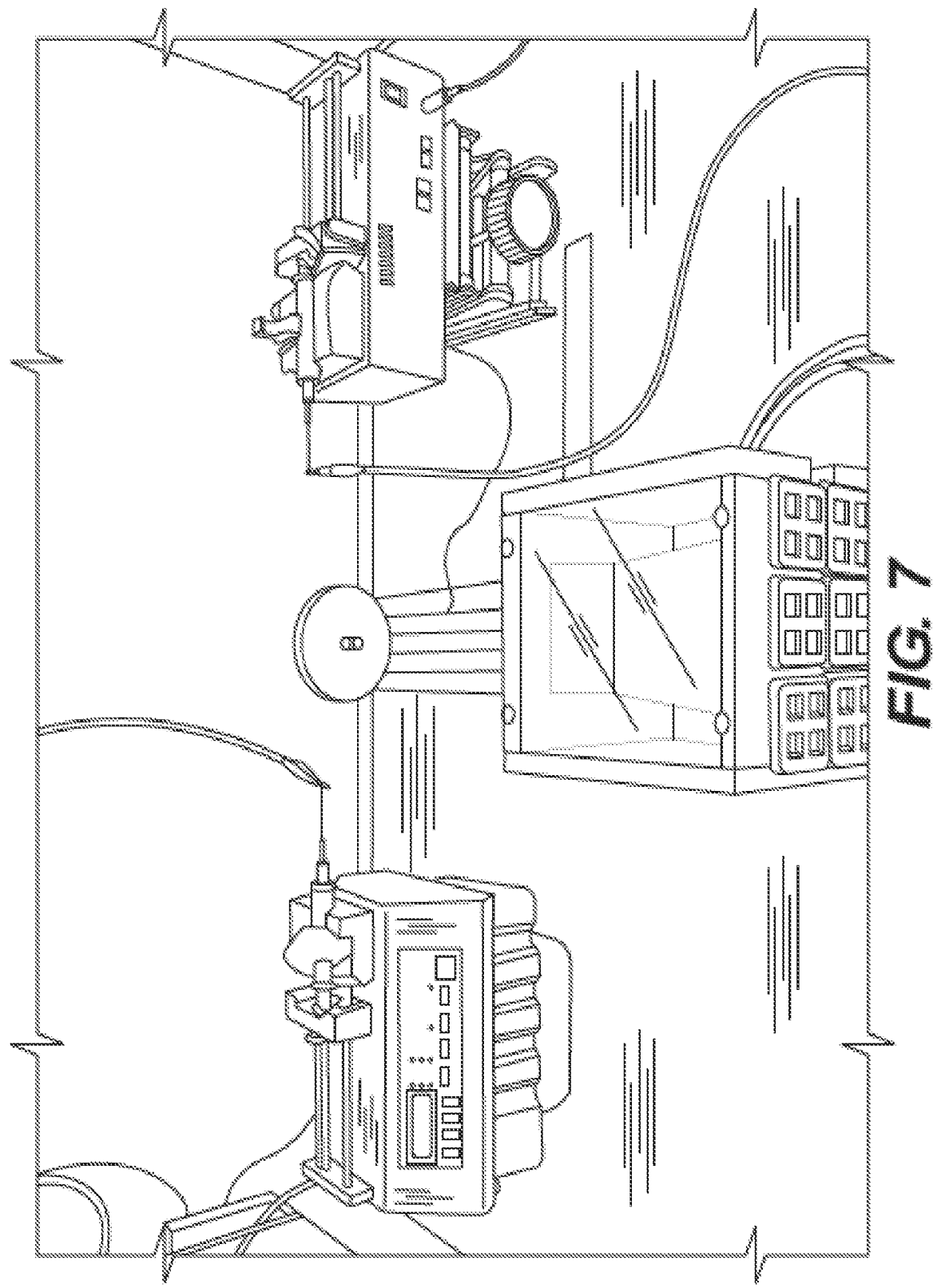
FIG. 7 depicts two syringes pumps with basement membrane, each attached to a high voltage power supply, with one supply set to positive (+) voltage, the other set to negative (−) voltage to generate the static electric field for electrospinning, with fibers collected on the rotating or static charged rods, which are earthed in this schema. The charges of equal voltage and opposite charge combine in space above the dual charged rod mandrel in a the vortex of the electric field, depositing as charge neutralized fibers on the rods, which allows for enhanced thickness of the collected aligned fibers over conventional methods.
Figure 8:
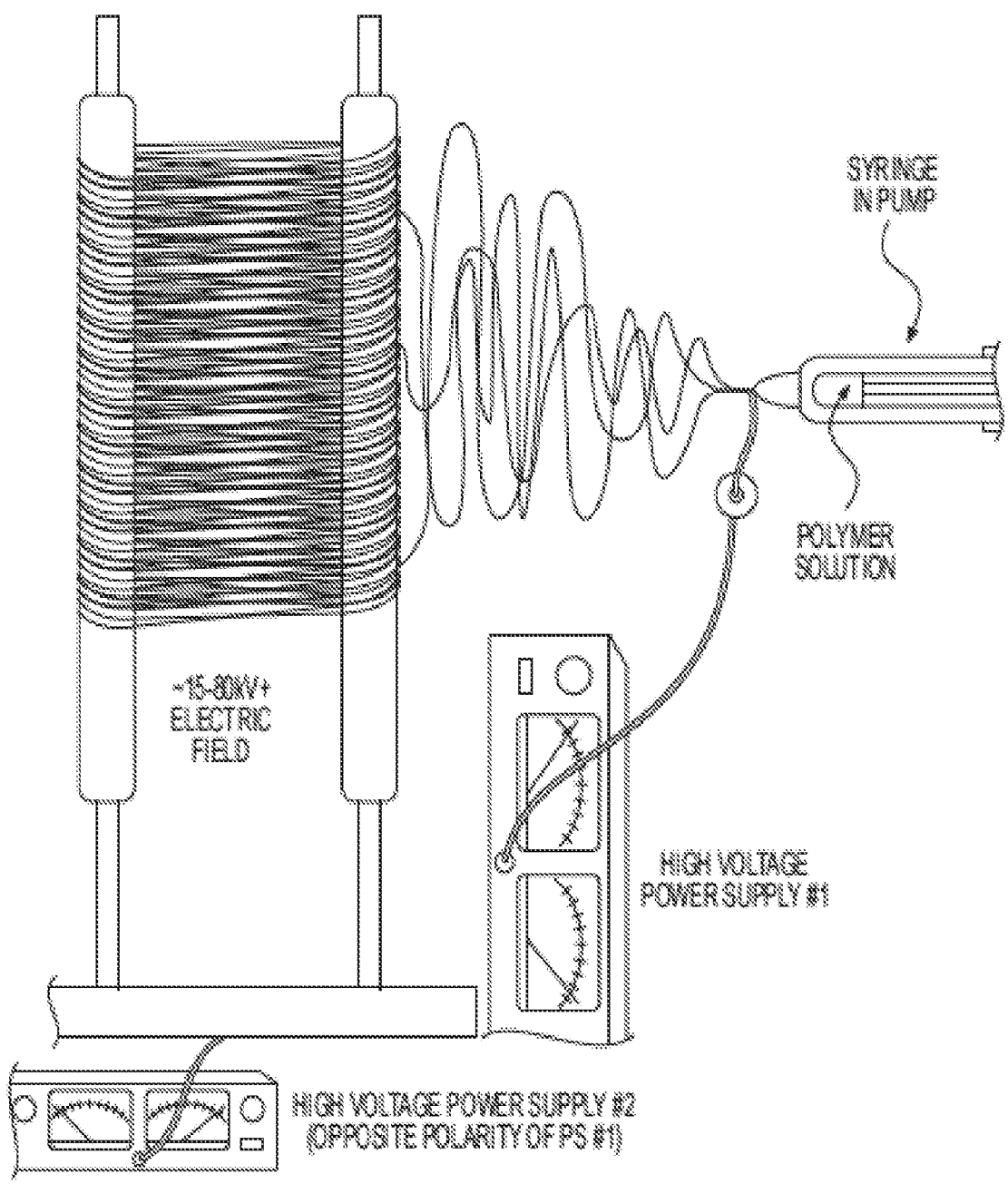
FIG. 8 also depicts exemplary elements of the rotating parallel electric charged rod electrospinning setup.

FIG. 5 illustrates a design for rotating the charged parallel rods using a mercury coupled bearing to allow electrical conductance with the rotating charged rods mounted in plastic platforms attaching to a high speed electrical motor (0-4000 RPMs). The actual implementation of this rotating rod design is shown in FIG. 6 along with a picture of a sheet of aligned fibers formed in this fashion for reference. FIG. 7 shows a slight modification of this rotating charged parallel point charged rod fiber alignment process whereby electrospun fibers of opposite charge are propelled towards each other in the static field, whereby the fibers combine in a "whirlpool" fashion roughly equidistant apart in space. In this arrangement, the fiber charges are effectively neutralized and the fibers are then collected on the grounded rotating rods of the mandrel, which allows a thicker layer of fibers to be collected due to less fiber-to-fiber charge repulsion. Equally charged fibers are believed to have a repulsive effect on each other in the collected fibers. Charge neutralization of the fibers in this fashion theoretically negates this phenomenon, which we appreciated as being able to electrospin sheets that are up to around 3.4 times the thickness of conventionally electrospun fiber sheets. Another exemplary parallel electric charged rod electrospinning setup is shown in FIG. 8.

By implementing a pneumatic motor in the conformations for electrospinning aligned (and random) nanofibers onto a mandrel as described above, on average 9.24% more material is collected on the mandrel(s) compared to using an electrical motor.

The invention claimed is:

1. An electrospinning apparatus comprising:
   (i) at least one spinneret comprising an electrified tip configured to extrude a solution from a reservoir to provide electrospun fibers; and
   (ii) a collector comprising a bone graft implant, and including at least two rods and a platform configured to support and connect to the at least two rods,
   wherein the two rods are configured to split an electric field between them, and the electrospun fibers are collected on a surface of the bone graft implant.

2. The electrospinning apparatus of claim 1, wherein the split electric field is separated by an air insulator.

3. The electrospinning apparatus of claim 1, wherein the two rods are electrified with an opposite charge from the electrified tip.

4. The electrospinning apparatus of claim 1, wherein the two rods are separated from one another by about 1 cm or more.

5. The electrospinning apparatus of claim 1, wherein the two rods are separated from one another from about 1 cm to about 25 cm.

6. The electrospinning apparatus of claim 1, wherein the two rods are separated from one another from about 10 cm to about 20 cm.

7. The electrospinning apparatus of claim 1, wherein the two rods are grounded.

8. The electrospinning apparatus of claim 1, wherein the platform is configured to spin resulting in rotation of the two rods about the spinning axis of the platform.

9. The electrospinning apparatus of claim 8, wherein the platform comprises a bearing connected to the two rods.

10. The electrospinning apparatus of claim 9, wherein the bearing comprises an electrical conductor configured to allow electrical conductance to the two rods.

11. The electrospinning apparatus of claim 9, wherein the bearing comprises mercury.

12. The electrospinning apparatus of claim 8, wherein the two rods are configured to rotate at between 0 and 8000 RPM.

13. The electrospinning apparatus of claim 12, wherein the two rods are configured to rotate at between 0 and 4000 RPM.

14. The electrospinning apparatus of claim 1, wherein the two rods are stationary.

15. The electrospinning apparatus of claim 1, wherein the spinneret is selected from the group consisting of a multiple nozzle spinneret, a single syringe or capillary spinneret, and a compound spinneret.

16. The electrospinning apparatus of claim 1, wherein the spinneret is a single syringe or capillary spinneret.

17. The electrospinning apparatus of claim 1, further comprising a chamber enclosing the spinneret and the collector.

18. The electrospinning apparatus of claim 1, further comprising a control mechanism configured to control the electric potential of the electrified tip.

19. The electrospinning apparatus of claim 1, further comprising an electric source connected to the electrified tip.

20. The electrospinning apparatus of claim 1, wherein the collector has only two rods.

21. The electrospinning apparatus of claim 1, further comprising a pneumatic motor configure to rotate the two rods.

22. The electrospinning apparatus of claim 1, wherein the rod is a bar of material having a shape including at least one of a prism, a cylinder, a pentagonal rod, a square rod, or a triangular rod.

23. The electrospinning apparatus of claim 1, wherein the bone graft implant is an allograft.

24. The electrospinning apparatus of claim 1, wherein the bone graft implant is a xenograft.

25. The electrospinning apparatus of claim 1, wherein the bone graft implant is a monolithic spinal implant.

26. The electrospinning apparatus of claim 1, wherein the bone graft implant is a composite spinal implant.

27. A method of preparing an electrospun fiber by electrospinning using the electrospinning apparatus according to claim 1, comprising (i) extruding one or more solution from the electrified tip of the spinneret, and (ii) collecting the extruded solution on a part of the collector.

\* \* \* \* \*